United States Patent [19]

Schmidt et al.

[11] 4,363,503
[45] Dec. 14, 1982

[54] PYRIDINE COLOR FORMERS

[75] Inventors: Paul J. Schmidt, Sharonville; William M. Hung, Cincinnati, both of Ohio

[73] Assignee: Sterling Drug Inc., New York, N.Y.

[21] Appl. No.: 243,798

[22] Filed: Mar. 16, 1981

[51] Int. Cl.$^3$ .................. B41M 5/16; B41M 5/18; B41M 5/22

[52] U.S. Cl. .................. 282/27.5; 427/151; 428/320.4; 428/320.6; 428/320.8; 428/488; 428/537; 428/913; 428/914; 546/329

[58] Field of Search .................. 106/21; 546/15, 16, 546/250, 268, 269, 272–274, 283, 284, 329; 282/27.5; 427/150–153; 428/320.4, 320.6, 320.8, 488, 537, 913, 914

[56] References Cited

U.S. PATENT DOCUMENTS 3,985,376  10/1976  Baumann et al. .................. 282/27.5

OTHER PUBLICATIONS

R. L. Frank et al., J. Amer. Chem. Soc. 71, 2629–2635 (1949).
M. Weiss, J. Amer. Chem. Soc. 74, 200–202 (1952).
E. Koenigs et al., Ann. 509, 142–158 (1934).
H. Gilman et al., J. Org. Chem. 22, 1169–1171 (1957).

*Primary Examiner*—Bruce H. Hess
*Attorney, Agent, or Firm*—Paul E. Dupont; B. Woodrow Wyatt

[57] ABSTRACT

Novel 4-aryl-or heteroaryl-2,6-bis[(substituted-amino)-phenyl]pyridines which are useful as color formers in pressure-sensitive carbonless duplicating systems and thermal marking systems are prepared by reacting a 2-, 3- or 4-$R_1R_2N$-acetophenone with an aryl or heteroaryl aldehyde in the present of ammonia or an ammonia-releasing agent.

5 Claims, No Drawings

PYRIDINE COLOR FORMERS

BACKGROUND OF THE INVENTION

1. Field of the Invention

This invention relates to a group of compounds classified in the field of organic chemistry as 4-aryl or heteroaryl-2,6-bis[(substituted-amino)phenyl]pyridines useful as color formers in pressure-sensitive carbonless duplicating systems and thermal marking systems, to a process for the preparation thereof and to pressure-sensitive carbonless duplicating systems and thermal marking systems containing the same.

2. Description of the Prior Art

Several classes of organic compounds of widely diverse structural types are known to be useful as color formers for carbonless duplicating systems. Among the more important classes are the phenothiazines, for example N-benzoyl leuco methylene blue; fluorans, for example 2'-anilino-6'-diethylaminofluoran; phthalides, for example crystal violet lactone; arylsulfinate salts of Michler's Hydrol; substituted phenylpyridines and various other types of colorless precursors currently employed in commercially accepted carbonless copy systems. Typical of the many such systems taught in the prior art are those described in U.S. Pat. Nos. 2,712,507, 2,800,457, 3,041,289 and 4,000,087, which issued July 5, 1955, July 23, 1957, June 26, 1962 and Dec. 28, 1976, respectively. Many of the color formers in the prior art suffer one or more disadvantages such as low tinctorial strength, poor light stability, poor xerographic copiability and low solubility in common organic solvents, the latter disadvantage thus requiring the use of specialized and expensive solvents in order to obtain microencapsulated solutions of sufficient concentration for use in pressure-sensitive copy systems.

The following appear to constitute the most pertinent prior art relative to the present invention.

Baumann et al., U.S. Pat. No. 3,985,376, patented Oct. 12, 1976 disclose compounds of the formula:

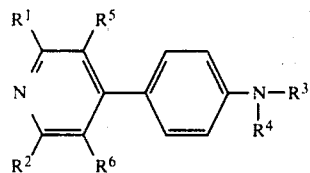

in which
- $R^1$ and $R^2$ are hydrogen or alkyl or aryl of one to eight carbon atoms which may bear alkoxy or halogen as a substituent;
- $R^3$ is hydrogen or alkyl of one to five carbon atoms;
- $R^4$ is alkyl, haloalkyl, cyanalkyl, aryl or aralkyl of one to eight carbon atoms which may bear alkoxy as a substituent;
- $R^5$ and $R^6$ are hydrogen or carbalkoxy of two to five carbon atoms and $R^3$ and $R^4$ may be closed to form a ring. Specific compounds disclosed are those wherein $R^1$ and $R^2$ are each phenyl, $R^5$ and $R^6$ are each hydrogen, $R^3$ is methyl and $R^4$ is methyl, phenyl or p-ethoxyphenyl, and also those wherein $R^1$ and $R^2$ are each p-methoxyphenyl, $R^5$ and $R^6$ are each hydrogen and $R^3$ and $R^4$ are each methyl. The compounds are stated to be useful as dye precursors for pressure-sensitive recording material.

Frank and Seven, J. Amer. Chem. Soc. 71, 2629–2635 (1949) disclose 4-(p-chlorophenyl)-2,6-diphenylpyridine, 4-anisyl-2,6-diphenylpyridine and 2,6-diphenyl-4-(m-methoxyphenyl)pyridine. These compounds were isolated as reaction products in a study of the Chichibabin reaction.

M. Weiss, J. Amer. Chem. Soc. 74, 200–202 (1952) discloses in most pertinent part compounds of the formula

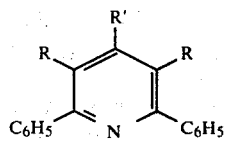

wherein R is hydrogen, and R' is phenyl, 4-methoxyphenyl, 3,4-methylenedioxyphenyl, 4-dimethylaminophenyl or 2-methoxyphenyl. These compounds were isolated as reaction products in a study of the Chichibabin synthesis.

E. Koenigs and E. Ruppelt, Ann. 509, 142–158 (1934) disclose as basic dyestuffs a number of 4-[p-dialkylaminophenyl]-pyridines.

Gilman et al., J. Org. Chem. 22, 1169–1171 (1957) in most pertinent part disclose 2,6-bis(p-diethylaminophenyl)-pyridine as a relatively weak liquid scintillator solute.

3. Prior Publications

The following United Kingdom patent application was published prior to the filing of applicants' instant application but subsequent to the completion of applicants' invention.

United Kingdom patent application No. 2,029,591A, published Mar. 19, 1980 discloses pyridine derivatives having the formula

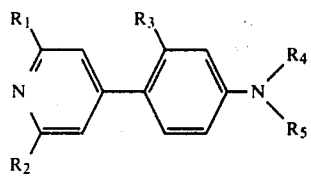

wherein
- $R_1$ and $R_2$ are independently hydrogen, phenyl group or chlorine-substituted phenyl groups;
- $R_3$ is hydrogen, lower-alkyl groups or lower-alkoxy groups;
- $R_4$ and $R_5$ are independently lower-alkyl groups, benzyl group or phenyl group, said lower-alkyl groups possibly being substituted with a cyano group, a chlorine atom or a lower-alkoxy group. The compounds are stated to produce a yellow color on heating in the presence of an electron acceptor.

SUMMARY OF THE INVENTION

The present invention provides novel 4-aryl- or heteroaryl-2,6-bis[(substituted-amino)phenyl]pyridines useful as color formers in pressure-sensitive carbonless duplicating systems and thermal marking systems. The compounds develop light-stable colored images of good tinctorial strength, and are soluble in common organic solvents. Moreover, because the compounds produce yellow to orange colors, they are especially valuable as toners used in admixture with other color formers to produce images of a neutral shade. The invention also provides a process for the preparation of these compounds as well as pressure-sensitive carbonless duplicating systems and thermal marking systems containing them.

In a composition of matter aspect the invention relates to a series of 4-aryl- or heteroaryl-2,6-bis(2-,3- or 4-$R_1R_2$N-phenyl)pyridines which are useful as color formers in pressure-sensitive carbonless duplicating systems and thermal marking systems.

In a process aspect, the present invention provides a process for preparing 4-aryl- or heteroaryl-2,6-bis(2-,3- or 4-$R_1R_2$N-phenyl)pyridines which comprises reacting a 2-,3- or 4-$R_1R_2$N-acetophenone with an aryl or heteroaryl aldehyde in the presence of ammonia or an ammonia-releasing agent.

In an article of manufacture aspect the present invention relates to a pressure-sensitive carbonless duplicating system or thermal marking system containing a color-forming substance comprising at least one of the 4-aryl- or heteroaryl-2,6-bis[(substituted-amino)-phenyl]pyridines of the invention.

DETAILED DESCRIPTION OF THE INVENTION INCLUSIVE OF THE PREFERRED EMBODIMENTS

In a composition of matter aspect the invention sought to be patented resides in a compound having Formula I hereinbelow:

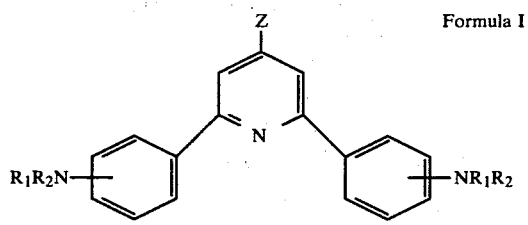

Formula I wherein:
$R_1$ and $R_2$ are the same or different and are selected from the group consisting of lower-alkyl and benzyl, or
$NR_1R_2$ is pyrrolidinyl, piperidinyl or morpholinyl;
Z is naphthyl, 9-julolidinyl or a substituent having the formula:

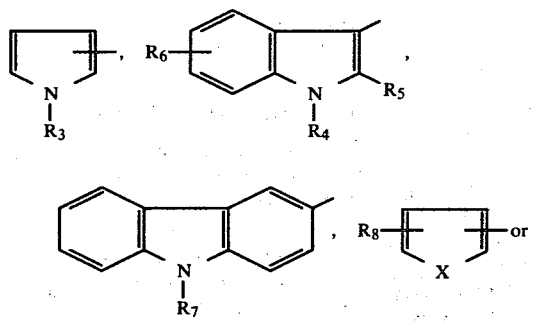

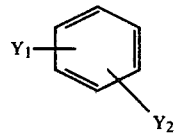

wherein:
$R_3$, $R_4$, $R_7$ and $R_8$ are hydrogen or non-tertiary lower-alkyl;
$R_5$ is hydrogen, phenyl or non-tertiary lower-alkyl;
$R_6$ is hydrogen, non-tertiary lower-alkyl or non-tertiary lower-alkoxy;
X is O or S;
$Y_1$ and $Y_2$ are the same or different and are selected from the group consisting of hydrogen, lower-alkyl, lower-alkoxy, halo, nitro, lower-alkoxycarbonyl, phenyl or $NR_9R_{10}$;
$R_9$ is lower-alkyl or benzyl;
$R_{10}$ is lower-alkyl, benzyl, cyano-lower-alkyl, or $NR_9R_{10}$ is pyrrolidinyl, piperidinyl, morpholinyl or isoindolinyl.

These compounds are useful as color formers for pressure-sensitive carbonless duplicating systems and thermal marking systems.

A particular embodiment sought to be patented resides in a compound having Formula I hereinabove wherein $R_1$ and $R_2$ have the previously given meanings and Z is a substituent having the formula

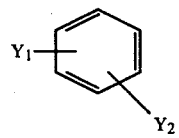

Preferred compounds within the ambit of this embodiment are those wherein $Y_1$ and $Y_2$ are the same or different and are selected from the group consisting of hydrogen, lower-alkyl and lower-alkoxy and where $R_1$ and $R_2$ are each lower-alkyl, especially 2,6-bis[4-(dimethylamino)phenyl]-4-phenylpyridine, 2,6-bis[4-(dimethyl)phenyl]-4-(4-methylphenyl)pyridine and 2,6-bis[4-(dimethylamino)phenyl]-4-(4-methoxyphenyl)pyridine.

Also preferred are the compounds wherein $R_1$ and $R_2$ are each lower-alkyl and one of $Y_1$ and $Y_2$ is $NR_9R_{10}$, $R_9$ and $R_{10}$ each being lower-alkyl, especially 2,4,6-tris[4-(dimethylamino)phenyl]pyridine. These compounds are particularly valuable because they are easily prepared from inexpensive and readily available starting materials.

In its process aspect, the invention sought to be patented resides in a process for preparing the compounds of Formula I hereinabove which comprises reacting approximately 2 molar equivalents of an acetophenone having Formula II hereinbelow:

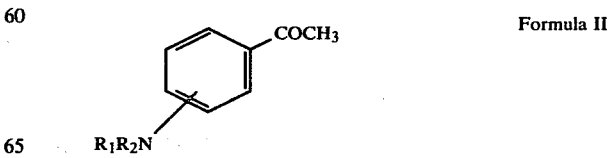

Formula II with approximately 1 molar equivalent of an aryl or heteroaryl aldehyde having Formula III hereinbelow:

Z—CHO                                      Formula III in the presence of ammonia or an ammonia-releasing agent where in Formulas II and III, $R_1$, $R_2$ and Z have the previously given meanings.

In an article of manufacture aspect the invention sought to be patented resides in a pressure-sensitive carbonless duplicating system or thermal marking system containing a support sheet coated with a color-forming substance comprising a compound having Formula I hereinabove.

A particular embodiment sought to be patented resides in a pressure-sensitive transfer sheet adapted for use with a receiving sheet having an electron-accepting layer comprising a support sheet coated on one side with a layer of pressure-rupturable microcapsules, said microcapsules containing a liquid solution of a color-forming substance comprising at least one compound having Formula I.

Another particular embodiment sought to be patented resides in a heat-responsive record material comprising a support sheet coated on one side with a layer containing a mixture comprising at least one color-forming compound having Formula I and an acidic developer arranged such that application of heat will produce a mark-forming reaction between the color-forming compound and the acidic developer.

A further embodiment sought to be patented resides in a pressure-sensitive carbonless duplicating system or a thermal marking system containing a support sheet coated with a color-forming substance comprising a compound having Formula I hereinabove in combination with a blue or green and a red or orange color former.

Preferred articles within the ambit of the particular embodiments above-described are those having a color-forming component of Formula I hereinabove in which $R_1$ and $R_2$ have the previously given meanings and Z is a substituent having the formula

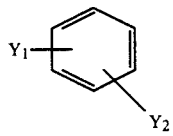

especially where $Y_1$ and $Y_2$ are the same or different and are selected from the group consisting of hydrogen, lower-alkyl and lower-alkoxy or where one of $Y_1$ and $Y_2$ is di-lower-alkylamino and where $R_1$ and $R_2$ are each lower-alkyl.

As used herein the term "halo" includes fluoro, chloro, bromo and iodo.

In the terms "lower-alkyl," "cyano-lower-alkyl," "lower-alkoxy" and "lower-alkoxycarbonyl," "lower-" denotes a saturated acyclic alkyl moiety having from 1 to 4 carbon atoms such as methyl, ethyl, propyl, isopropyl, butyl, sec-butyl or isobutyl.

The term "9-julolidinyl," of course, refers to the radical having the formula

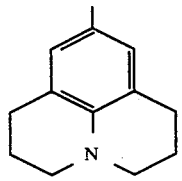

In accordance with the process aspect of this invention the compounds having Formula I hereinabove are obtained by reacting approximately two molar equivalents of an acetophenone of Formula II hereinabove with approximately one molar equivalent of an aryl or heteroaryl aldehyde of Formula III hereinabove in the presence of ammonia or an ammonia-releasing agent. Thus, the acetophenone and aldehyde can be condensed in the presence of aqueous or alcoholic ammonia or alternatively, and preferably, in the presence of an ammonia-releasing agent such as ammonium acetate in acetic acid. The reactants are heated at about 50°–150° C. for approximately 1 to 5 hours, usually at the reflux temperature of the solvent for about 2 hours. The product thus obtained can be isolated by filtration if it is insoluble in the reaction medium, or by dilution of the reaction medium with a miscible solvent in which the product is insoluble such as water or a lower-alkanol, for example, isopropyl alcohol, or a mixture of these in order to effect precipitation of the product. Alternatively, the reaction mixture can be poured into water or dilute ammonium hydroxide and the product extracted with an organic solvent such as benzene toluene or chloroform followed by evaporation of the organic solvent leaving the product as a residue. Frequently the product begins to separate from the reaction mixture as an oil. Usually the addition of a lower-alkanol such as ethanol or isopropyl alcohol to the hot reaction will induce the product to separate in crystalline form on cooling. The product once isolated can be purified by conventional means such as trituration or recrystallization from a suitable solvent.

The acetophenones of Formula II and the aldehydes of Formula III which are required as starting materials in the preparation of the final products of Formula I are generally known and are either commercially available or readily obtained by conventional procedures well known in the art. Those acetophenones and aldehydes which are specifically novel can be prepared in accordance with the procedures described for preparation of the known compounds.

The novel compounds of Formula I hereinabove are pale yellow to colorless in the depicted form. When contacted with an acidic medium, for example silica gel, or one of the types ordinarily employed in pressure-sensitive carbonless duplicating systems such as silton clay or phenolic resins, the compounds of Formula I develop an intense yellow to orange image which is xerographically copiable and light stable. The compounds are thus highly suitable for use as color precursors, that is, color-forming substances in pressure-sensitive carbonless duplicating systems. Because they produce a yellow to orange color, these compounds are especially valuable as toners which are used in admixture with other color formers to produce images of a neutral shade which desirably possess excellent xerographic copiability. Thus, a yellow to orange color former of Formula I hereinabove can be combined with a red or orange color former and a blue or green color former to afford a color-forming substance which produces a neutral or black image.

The compounds of this invention may be incorporated in any of the commercially accepted systems known in the carbonless duplicating art. A typical technique for such application is as follows: solutions containing one or more color precursor compounds of Formula I, optionally in admixture with other color formers as noted above, in suitable solvents are microencapsulated by well-known procedures, for example as described in U.S. Pat. Nos. 3,649,649, 3,429,827 and 4,000,087. The microcapsules are coated on the reverse side of a transfer sheet with the aid of a suitable binder and the coated transfer sheet is then assembled in a manifold with the microcapsule-coated side in contact with a receiving sheet coated with an electron accepting substance for example silton clay or phenolic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon forms a colored image. It is, of course, obvious that variants of this mode of application can be utilized. For example, the receiving sheet in a manifold can alternatively be coated with the subject compounds and the acidic developing agent can be contained in microcapsules applied on the reverse side of the top sheet in the manifold; or the receiving sheet can be coated with a mixture containing both the acidic developing agent and the microencapsulated color former.

It has also been found that when the compounds of Formula I are intimately mixed with an acidic developer of the type generally employed in thermal papers such as described in U.S. Pat. Nos. 3,539,375 and 3,447,944, that is, papers which produce a colored image when contacted with a heated stylus or heated type, for example, bisphenol A, heating of the mixture produces a colored image of varying shades from yellow to orange depending on the particular compound of the invention employed. As noted above, darker shades can be produced by mixing the compounds of Formula I with other color formers. The ability of the compounds of Formula I to form an intense color when heated in admixture with an acidic developer such as bisphenol A makes them useful in thermal paper marking systems either where an original or duplicate copy is prepared by contacting the thermal paper with a heated stylus or heated type in any of the methods generally known in the art.

The molecular structure of the compounds of this invention were assigned on the basis of the modes of synthesis, elemental analysis and study of their infrared and nuclear magnetic resonance spectra.

The following examples will further illustrate the invention without however limiting it thereto.

EXAMPLE 1

A mixture containing 4.2 g. of 4-anisaldehyde, 9.8 g. of 4-(dimethylamino)acetophenone, 36 g. of ammonium acetate and 50 ml. of glacial acetic acid was refluxed for one hour and was then allowed to stand at room temperature overnight. The mixture was filtered and the collected solid was washed with isopropanol and water. The solid was then slurried in 100 ml. of hot isopropanol. After cooling to room temperature, the pale yellow solid was collected, washed with isopropanol and dried to give 3.9 g. of 4-(4-methoxyphenyl)-2,6-bis[4-(dimethylamino)phenyl]pyridine, m.p. 194°–197° C. This product produced an orange image on contact with acidic clay or phenolic resin.

EXAMPLE 2

A mixture containing 3.2 g. of benzaldehyde, 9.8 g. of 4-(dimethylamino)acetophenone, 30 g. of ammonium acetate and 75 ml. of glacial acetic acid was refluxed for two hours. After cooling to room temperature, the reaction mixture was poured into 300 ml. of toluene and 400 ml. of 5% aqueous ammonium hydroxide. The toluene layer was separated, washed successively with water and saturated aqueous sodium chloride and evaporated to dryness under vacuum. The residue was slurried in ethanol and collected by filtration to give 2.1 g. of 4-phenyl-2,6-bis[4-(dimethylamino)-phenyl]pyridine, as a pale yellow solid, m.p. 176°–179° C. A toluene solution of the product developed an orange image when contacted with acidic clay and a yellow image when contacted with phenolic resins.

EXAMPLE 3

Following a procedure similar to that described in Example 1 but employing 4.0 g. of 4-methylbenzaldehyde, 9.8 g. of 4-(dimethylamino)acetophenone, 35 g. of ammonium acetate and 40 ml. of glacial acetic acid there was obtained 3.8 g. of 4-(4-methylphenyl)-2,6-bis[4-(dimethylamino)phenyl]pyridine, as a pale greenish yellow solid, m.p. 210°–222° C. This product produced an orange image on contact with acidic clay or phenolic resin.

EXAMPLE 4

Following a procedure similar to that described in Example 2 but employing 4.5 g. of 4-(dimethylamino)-benzaldehyde, 9.8 g. of 4-(dimethylamino)acetophenone, 30 g. of ammonium acetate and 75 ml. of glacial acetic acid there was obtained 2.3 g. of 2,4,6-tris[4-(dimethylamino)phenyl]pyridine, as a yellow solid, m.p. 256°–260° C. This product produced a yellow image on contact with acidic clay or phenolic resin.

EXAMPLE 5

Following a procedure similar to that described in Example 2 but employing 4.2 g. of 4-chlorobenzaldehyde, 9.8 g. of 4-(dimethylamino)acetophenone, 36 g. of ammonium acetate and 50 ml. of glacial acetic acid there was obtained 2.4 g. of 4-(4-chlorophenyl)-2,6-bis[4-(dimethylamino)phenyl]pyridine, as a pale yellow solid, m.p. 178°–182° C. This product produced a yellowish-orange image on contact with acidic clay or phenolic resin.

EXAMPLE 6

Following a procedure similar to that described in Example 2 but employing 5.5 g. of 2-chloro-4-(dimethylamino)benzaldehyde, 9.8 g. of 4-(dimethylamino)acetophenone, 35 g. of ammonium acetate and 50 ml. of glacial acetic acid there was obtained 3.4 g. of 4-[2-chloro-4-(dimethylamino)phenyl]-2,6-bis[4-dimethylamino)phenyl]pyridine, as a pale yellow solid, m.p. 131°–139° C. The product produced a yellow image on contact with acidic clay or phenolic resin.

EXAMPLE 7

Following a procedure similar to that described in Example 1 but employing 4.5 g. of 4-nitrobenzaldehyde, 9.8 g. of 4-(dimethylamino)acetophenone, 35 g. of ammonium acetate and 50 ml. of glacial acetic acid there was obtained 5.5 g. of 4-(4-nitrophenyl)-2,6-bis[4-(dimethylamino)phenyl]pyridine, as a yellow solid, m.p. 156°–164° C. This product produced an orange image on contact with acidic clay or phenolic resin.

EXAMPLE 8

Following a procedure similar to that described in Example 2 but employing 5.6 g. of 4-[(2-cyanoethyl)methylamino]-benzaldehyde, 9.8 g. of 4-(dimethylamino)acetophenone, 40 g. of ammonium acetate and 35 ml. of glacial acetic acid there was obtained 3.5 g. of 4-[4-[(2-cyanoethyl)methylamino]phenyl]-2,6-bis[4-(dimethylamino)phenyl]pyridine, as a light yellow solid, m.p. 170°–174° C. This product produced an orange-yellow image on contact with acidic clay or phenolic resin.

EXAMPLE 9

Following a procedure similar to that described in Example 2 but employing 5.0 g. of 2,5-dimethoxybenzaldehyde, 9.8 g. of 4-(dimethylamino)acetophenone, 40 g. of ammonium acetate and 30 ml. of glacial acetic acid, there was obtained 2.5 g. of 4-(2,5-dimethoxyphenyl)-2,6-bis[4-(dimethylamino)phenyl]pyridine, as a light yellow solid, m.p. 199°–206° C. This product produced a yellowish orange image on contact with acidic clay or phenolic resin.

EXAMPLE 10

A mixture containing 4.5 g. of 3-nitrobenzaldehyde, 9.8 g. of 4-(dimethylamino)acetophenone, 40 g. of ammonium acetate and 40 ml. of glacial acetic acid was refluxed for two hours. After cooling to room temperature, the resulting tarry solid was collected and was first slurried in isopropanol then in toluene to give 3.0 g. of 4-(3-nitrophenyl)-2,6-bis[4-(dimethylamino)-phenyl]-pyridine, as a yellow solid, m.p. 194°–200° C. This product produced a yellowish-orange image on contact with acidic clay or phenolic resin.

EXAMPLE 11

A mixture containing 4.6 g. of methyl 4-formylbenzoate, 9.8 g. of 4-(dimethylamino)acetophenone, 40 g. of ammonium acetate and 30 ml. of glacial acetic acid was heated 3 hours under reflux. The mixture was cooled to 70° C. and 75 ml. of isopropanol was added, reheated to 90°–95° C. and held for 30 minutes. After cooling to room temperature, the yellow solid was collected, washed with isopropanol and dried to give 3.9 g. of 4-[4-(methoxycarbonyl)-phenyl]-2,6-bis[4-(dimethylamino)phenyl]pyridine, m.p. 244°–250° C. This product produced an orange image on contact with acidic clay or phenolic resin.

EXAMPLE 12

Following a procedure similar to that described in Example 2 but employing 5.4 g. of 4-(diethylamino)benzaldehyde, 9.8 g. of 4-(dimethylamino)acetophenone, 30 g. of ammonium acetate and 75 ml. of glacial acetic acid there was obtained 1.0 g. of 4-[4-(diethylamino)phenyl]-2,6-bis[4-(dimethylamino)phenyl]pyridine as a yellow solid, m.p. 193.9°–201.8° C. A toluene solution of the product developed an orange image when contacted with acidic clay and a yellow image when contacted with phenolic resin.

EXAMPLE 13

Following a procedure similar to that described in Example 1 but employing 4.0 g. of 4-biphenylcarboxaldehyde, 6.5 g. of 4-(dimethylamino)acetophenone, 27 g. of ammonium acetate and 25 ml. of glacial acetic acid there was obtained 3.0 g. of 4-(4-biphenylyl)-2,6-bis[4-(dimethylamino)phenyl]pyridine, as a yellow solid, m.p. 213°–216° C. This product produced an orange image on contact with acidic clay or phenolic resin.

EXAMPLE 14

Following a procedure similar to that described in Example 1 but employing 4.7 g. of 1-naphthaldehyde, 9.8 g. of 4-(dimethylamino)acetophenone, 40 g. of ammonium acetate and 35 ml. of glacial acetic acid there was obtained 3.6 g. of 4-(1-naphthyl)-2,6-bis[4-(dimethylamino)phenyl]pyridine, as a light yellow solid, m.p. 189°–208° C. A chloroform solution of the product developed an orange image when contacted with acidic clay and a yellow image when contacted with phenolic resin.

EXAMPLE 15

Following a procedure similar to that described in Example 2 but employing 6.0 g. of 4-(1-pyrrolidinyl)-benzaldehyde, 11 g. of 4-(dimethylamino)acetophenone, 40 g. of ammonium acetate and 50 ml. of glacial acetic acid there was obtained 4.7 g. of 4-[4-(1-pyrrolidinyl)phenyl]-2,6-bis[4-(dimethylamino)phenyl]-pyridine, as a yellow solid, m.p. 199.8°–214.9° C. This product produced a yellow image on contact with acidic clay or phenolic resin.

EXAMPLE 16

Following a procedure similar to that described in Example 1 but employing 6.3 g. of 4-(1-piperidinyl)benzaldehyde, 11 g. of 4-(dimethylamino)acetophenone, 40 g. of ammonium acetate and 50 ml. of glacial acetic acid there was obtained 5.2 g. of 4-[4-(1-piperidiny)phenyl]-2,6-bis[4-(dimethylamino)phenyl]pyridine as a yellow solid, m.p. 217.5°–220.9° C. A chloroform solution of the product developed an orange image when contacted with acidic clay and a yellow image when contacted with phenolic resin.

EXAMPLE 17

Following a procedure similar to that described in Example 1 but employing 5.6 g. of 4-(2-isoindolinyl)-benzaldehyde, 8.5 g. of 4-(dimethylamino)acetophenone, 40 g. of ammonium acetate and 50 ml. of glacial acetic acid there was obtained 4.0 g. of 4-[4-(2-isoindolinyl)phenyl]-2,6-bis[4-(dimethylamino)phenyl]pyridine, as a muddy yellow solid, m.p. 265°–271° C. A chloroform solution of the product developed an orange image when contacted with acidic clay and a yellow image when contacted with phenolic resin.

EXAMPLE 18

Following a procedure similar to that described in Example 11 but employing 3.0 g. of 4-(4-morpholinyl)-benzaldehyde, 5.0 g. of 4-(dimethylamino)acetophenone, 25 g. of ammonium acetate and 40 ml. of glacial acetic acid there was obtained 2.2 g. of 4-[4-(4-morpholinyl)phenyl]-2,6-bis[4-(dimethylamino)phenyl]- pyridine as a pale yellow solid, m.p. 231°–234° C. A chloroform solution of the product developed an orange image when contacted with acidic clay and a yellow image when contacted with phenolic resin.

EXAMPLE 19

Following a procedure similar to that described in Example 2 but employing 4.8 g. of 2-methyl-4-(1-pyrrolidinyl)benzaldehyde, 8.5 g. of 4-(dimethylamino)acetophenone, 40 g. of ammonium acetate and 50 ml. of glacial acetic acid there was obtained 2.6 g. of 4-[2-methyl-4-(1-pyrrolidinyl)phenyl]-2,6-bis[4-(dimethylamino)phenyl]pyridine, as a yellow solid, m.p. 225°–229° C. A chloroform solution of the product developed an orange image when contacted with acidic clay and a yellow image when contacted with phenolic resin.

EXAMPLE 20

Following a procedure similar to that described in Example 2 but employing 5.1 g. of 9-julolidinecarboxaldehyde, 8.2 g. of 4-(dimethylamino)acetophenone, 33 g. of ammonium acetate and 25 ml. of glacial acetic acid there was obtained 3.5 g. of 4-(9-julolidinyl)-2,6-bis[4-(dimethylamino)phenyl]pyridine, as an orange-yellow solid, m.p. 237°–249° C. This product produced a yellowish-orange image on contact with acidic clay or phenolic resin.

EXAMPLE 21

Following a procedure similar to that described in Example 11 but employing 5.1 g. of 4-anisaldehyde, 9.8 g. of 3-(dimethylamino)acetophenone, 40 g. of ammonium acetate and 35 ml. of glacial acetic acid there was obtained 2.5 g. of 4-(4-methoxyphenyl)-2,6-bis[3-(dimethylamino)phenyl]pyridine, as a milky white solid, m.p. 187°–189° C. This product produced a weak yellow image on contact with acidic clay or phenolic resin.

EXAMPLE 22

Following a procedure similar to that described in Example 2 but employing 3.2 g. of benzaldehyde, 9.8 g. of 3-(dimethylamino)acetophenone, 40 g. of ammonium acetate and 35 ml. of glacial acetic acid there was obtained 2.0 g. of 4-phenyl-2,6-bis[3-(dimethylamino)-phenyl]pyridine, as an off-white solid, m.p. 142°–147° C. This product produced a weak orange image on contact with acidic clay or phenolic resin.

EXAMPLE 23

Following a procedure similar to that described in Example 2 but employing 3.6 g. of 4-methylbenzaldehyde, 11.5 g. of 4-(diethylamino)acetophenone, 40 g. of ammonium acetate and 30 ml. of glacial acetic acid there was obtained 2.0 g. of 4-(4-methylphenyl)-2,6-bis[4-(diethylamino)phenyl]pyridine, as a yellow solid, m.p. 174°–178.5° C. This product produced an orange image on contact with acidic clay or phenolic resin.

EXAMPLE 24

Following a procedure similar to that described in Example 2 but employing 4.1 g. of 4-anisaldehyde, 11.5 g. of 4-(diethylamino)acetophenone, 40 g. of ammonium acetate and 30 ml. of glacial acetic acid there was obtained 2.0 g. of 4-(4-methoxyphenyl)-2,6-bis[4-(diethylamino)phenyl]pyridine as a brownish-yellow solid, m.p. 77°–87.5° C. This product produced a yellowish-orange image on contact with acidic clay or phenolic resin.

EXAMPLE 25

Following a procedure similar to that described in Example 11 but employing 4.1 g. of 4-anisaldehyde, 21 g. of 4-(dibenzylamino)acetophenone, 40 g. of ammonium acetate and 30 ml. of glacial acetic acid there was obtained 5.5 g. of 4-(4-methoxyphenyl)-2,6-bis[4-(dibenzylamino)phenyl]pyridine as a yellow solid, m.p. 72.3°–77.5° C. This product produced a yellow image on contact with acidic clay or phenolic resin.

EXAMPLE 26

Following a procedure similar to that described in Example 2 but employing 3.4 g. of 4-anisaldehyde, 10.2 g. of 4-(1-piperidinyl)acetophenone, 35 g. of ammonium acetate and 40 ml. of glacial acetic acid there was obtained 3.4 g. of 4-(4-methoxyphenyl)-2,6-bis[4-(1-piperidinyl)phenyl]pyridine, as an off-white solid, m.p. 114°–118° C. This product produced a yellow image on contact with acidic clay or phenolic resin.

EXAMPLE 27

A mixture containing 4.6 g. of 4-anisaldehyde, 14 g. of 4-(4-morpholinyl)acetophenone, 50 g. of ammonium acetate and 60 ml. of glacial acetic acid was refluxed for two hours. After cooling to room temperature, the solution was decanted and the residual tarry solid was washed with water and isopropanol. The tarry solid was then dissolved in 250 ml. of acetone and added dropwise to 1500 ml. of water and 25 g. of sodium chloride to yield 8.5 g. of 4-(4-methoxyphenyl)-2,6-bis[4-(4-morpholinyl)phenyl]pyridine as a pale yellow solid, m.p. 100°–110° C. This product produced a greenish-yellow image on contact with acidic clay or phenolic resin.

EXAMPLE 28

Following a procedure similar to that described in Example 1 but employing 4.1 g. of 4-fluorobenzaldehyde, 12.6 g. of 4-(1-pyrrolidinyl)acetophenone, 50 g. of ammonium acetate and 60 ml. of glacial acetic acid there was obtained 2.9 g. of 4-(4-fluorophenyl)-2,6-bis[4-(1-pyrrolidinyl)phenyl]pyridine as a light yellow solid, m.p. 207°–212° C. A chloroform solution of the product developed a reddish orange image when contacted with acidic clay and an orange image when contacted with phenolic resin.

EXAMPLE 29

Following a procedure similar to that described in Example 2 but employing 3.6 g. of 2-thiophenecarboxaldehyde, 9.8 g. of 4-(dimethylamino)acetophenone, 35 g. of ammonium acetate and 40 ml. of glacial acetic acid there was obtained 3.6 g. of 4-(2-thienyl)-2,6-bis[4-(dimethylamino)phenyl]pyridine as a straw-colored solid, m.p. 191°–198° C. This product produced an orange image on contact with acidic clay or phenolic resin.

EXAMPLE 30

Following a procedure similar to that described in Example 11 but employing 3.3 g. of N-methylpyrrole-2-carboxaldehyde 9.8 g. of 4-(dimethylamino)acetophenone, 40 g. of ammonium acetate and 30 ml. of glacial acetic acid there was obtained 1.5 g. of 4-(1-methylpyrrol-2-yl)-2,6-bis[4-(dimethylamino)phenyl]pyridine, as a greenish-yellow solid, m.p. 193°-200° C. This product produced a yellow image on contact with acidic clay or phenolic resin.

EXAMPLE 31

Following a procedure similar to that described in Example 11 but employing 3.3 g. of 5-methyl-2-furaldehyde, 9.8 g. of 4-(dimethylamino)acetophenone, 40 g. of ammonium acetate and 30 ml. of glacial acetic acid there was obtained 2.2 g. of 4-(5-methyl-2-furyl)-2,6-bis[4-(dimethylamino)phenyl]pyridine, as a yellow solid, m.p. 219.3°-225.5° C. This product produced an orange image on contact with acidic clay or phenolic resin.

EXAMPLE 32

Following a procedure similar to that described in Example 11 but employing 4.4 g. of indole-3-carboxaldehyde, 9.8 g. of 4-(dimethylamino)acetophenone, 40 g. of ammonium acetate and 30 ml. of glacial acetic acid there was obtained 4 g. of 4-(indol-3-yl)-2,6-bis[4-(dimethylamino)phenyl]pyridine, as a yellow solid, m.p. 237.2°-242.0° C. This product produced a yellowish-orange image on contact with acidic clay or phenolic resin.

EXAMPLE 33

Following a procedure similar to that described in Example 1 but employing 2.3 g. of N-ethyl-3-carbazolecarboxaldehyde, 3.3 g. of 4-(dimethylamino)acetophenone, 13.2 g. of ammonium acetate and 15 ml. of glacial acetic acid there was obtained 2.0 g. of 4-(9-ethylcarbazol-3-yl)-2,6-bis[4-(dimethylamino)-phenyl]pyridine as a yellow solid, m.p. 157°-173° C. This product produced an orange image on contact with acidic clay or phenolic resin.

EXAMPLE 34

Following a procedure similar to that described in Example 2 but employing 3.6 g. of indole-3-carboxaldehyde, 8.1 g. of 2-(dimethylamino)acetophenone, 34 g. of ammonium acetate and 30 ml. of glacial acetic acid there was obtained 3.1 g. of 4-(indol-3-yl)-2,6-bis[2-(dimethylamino)phenyl]pyridine, as a pale yellow solid, m.p. 230°-231° C. This product produced a yellow image on contact with acidic clay or phenolic resin.

EXAMPLE 35

Following a procedure similar to that described in Example 11 but employing 4.3 g. of indole-3-carboxaldehyde, 21 g. of 4-(dibenzylamino)acetophenone, 40 g. of ammonium acetate and 35 ml. of glacial acetic acid there was obtained 5.4 g. of 4-(indol-3-yl)-2,6-bis[4-(dibenzylamino)phenyl]pyridine, as a brownish-yellow solid, m.p. 105.0°-111.8° C. This product produced a yellow image on contact with acidic clay or phenolic resin.

EXAMPLE 36

Following a procedure similar to that described in Example 2 but employing 3.6 g. of indole-3-carboxaldehyde, 9.5 g. of 4-(1-pyrrolidinyl)acetophenone, 36 g. of ammonium acetate and 40 ml. of glacial acetic acid there was obtained 4.1 g. of 4-(indol-3-yl)-2,6-bis[4-(1-pyrrolidinyl)phenyl]pyridine, as a tan solid, m.p. 145°-147° C. This product produced a yellow image on contact with acidic clay or phenolic resin.

EXAMPLE 37

Following a procedure similar to that described in Example 1 but employing 3.8 g. of 2-thiophenecarboxaldehyde, 13.5 g. of 4-(1-piperidinyl)acetophenone, 50 g. of ammonium acetate and 60 ml. of glacial acetic acid there was obtained 4.3 g. of 4-(2-thienyl)-2,6-bis[4-(1-piperidinyl)phenyl]pyridine, as a light yellow solid, m.p. 198°-201° C. This product produced an orange color image on contact with acidic clay and phenolic resin.

EXAMPLE 38

Following a procedure similar to that described in Example 1 but employing 4.9 g. of indole-3-carboxaldehyde, 14 g. of 4-(4-morpholinyl)acetophenone, 50 g. of ammonium acetate and 60 ml. of glacial acetic acid there was obtained 7.7 g. of 4-(indol-3-yl)-2,6-bis[4-(4-morpholinyl)phenyl]pyridine, as a tan solid, m.p. 270°-275° C. This product produced a greenish yellow image on contact with acidic clay or phenolic resin.

EXAMPLE 39

Following a procedure similar to that described in Example 2 but employing 4.8 g. of 2,4-bis(dimethylamino)-benzaldehyde, 6.8 g. of 4-(dimethylamino)acetophenone, 33 g. of ammonium acetate and 25 ml. of glacial acetic acid there was obtained 0.3 g. of 4-[2,4-bis(dimethylamino)phenyl]-2,6-bis-[4-(dimethylamino)phenyl]pyridine, as a yellow solid, m.p. 235°-260° C. This product produced a yellowish orange image on contact with acidic clay or phenolic resin.

EXAMPLE 40

Following a procedure similar to that described in Example 2 but employing 11.5 g. of 2-ethoxy-4-(diethylamino)benzaldehyde, 16.3 g. of 4-(dimethylamino)acetophenone, 65 g. of ammonium acetate and 40 ml. of glacial acetic acid there was obtained 3.1 g. of 4-[2-ethoxy-4-(diethylamino)phenyl]-2,6-bis[4-(dimethylamino)phenyl]pyridine, as a yellow solid, m.p. 100°-110° C. This product produced a yellowish orange image on contact with acidic clay or phenolic resin.

EXAMPLE 41

Following a procedure similar to that described in Example 2 but employing 5.0 g. of 4-fluorobenzaldehyde, 13.0 g. of 4-(dimethylamino)acetophenone, 53 g. of ammonium acetate and 40 ml. of glacial acetic acid there was obtained 5.1 g. of 4-(4-fluorophenyl)-2,6-bis[4-(dimethylamino)phenyl]pyridine, as a greenish-yellow solid, m.p. 185°-187° C. This product produced a yellowish-orange image on contact with acidic clay or phenolic resin.

EXAMPLE 42

Following the procedure similar to that described in Example 11 but employing 5.5 g. of the ethyl ester of 5-(dimethylamino)-2-formuyl-benzoic acid, 8.1 g. of 4-(dimethylamino)-acetophenone, 30 g. of ammonium acetate and 25 ml. of glacial acetic acid there was obtained 2.7 g. of 4-[2-(ethoxycarbonyl)-4-(dimethylamino)phenyl]-2,6-bis[4-(dimethylamino)phenyl]-pyridine, as a yellow solid, m.p. 242.5°-252.5° C. This product produced a yellow image on contact with acidic clay or phenolic resin.

EXAMPLE 43

Following a procedure similar to that described in Example 2 but employing 4.4 g. of 1-ethyl-2-methylindole-3-carboxyaldehyde, 7.7 g. of 4-(dimethylamino)acetophenone, 30 g. of ammonium acetate and 25 ml. of glacial acetic acid there was obtained 2.8 g. of 4-(1-ethyl-2-methylindol-3-yl)-2,6-bis[4-(dimethylamino)phenyl]pyridine, as a light yellow solid, m.p. 216°–224° C. This product produced a yellow image on contact with acidic clay or phenolic resin.

EXAMPLE 44

A mixture containing 7.2 g. of 4-(benzylethylamino)benzaldehyde, 10.9 g. of 4-(dimethylamino)acetophenone, 40 g. of ammonium acetate and 25 ml. of glacial acetic acid was heated three hours at 125° C. After cooling to room temperature, the reaction mixture was diluted with water and extracted with toluene. The toluene extracts were washed with water followed by saturated aqueous sodium chloride and evaporated to dryness under vacuum. The residual oil was crystallized by repeated trituration first with hexane and then with isopropyl alcohol. The resulting solid was collected by filtration, washed with isopropyl alcohol and dried to give 4.2 g. of 4-[4-(benzylethylamino)phenyl]-2,6-bis[4-(dimethylamino)phenyl]pyridine, m.p. 157°–163.5° C. This product produced a yellow image on contact with acidic clay or phenolic resin.

It is contemplated that by following procedures similar to those described in Examples 1, 2, 10, 11, 27 and 44 but employing the appropriately substituted acetophenones and aryl or heteroaryl aldehydes of Formulas II and III, respectively, there will be obtained the 4-aryl- or heteroaryl-2,6-bis-[(substituted-amino)phenyl]pyridines of Formula I, Examples 45–57 presented in Table A below:

TABLE A

| Ex. | Z | $R_1$ | $R_2$ | Position of $NR_1R_2$ |
|---|---|---|---|---|
| 45 | $C_6H_5$ | $(CH_3)_2CH$ | $(CH_3)_2CH$ | 4 |
| 46 | $C_6H_5$ | $CH_3$ | $C_2H_5$ | 4 |
| 47 | $C_6H_5$ | $CH_3$ | $C_4H_9$ | 4 |
| 48 | $5\text{-}CH_3\text{—}2\text{-thienyl}$ | $CH_3$ | $CH_3$ | 4 |
| 49 | $4\text{-}(CH_3)_2CH\text{—}C_6H_4$ | $CH_3$ | $CH_3$ | 4 |
| 50 | $2\text{-}C_2H_5O\text{—}3\text{-}CH_3O\text{—}C_6H_3$ | $CH_3$ | $CH_3$ | 4 |
| 51 | $3\text{-Br—}C_6H_4$ | $CH_3$ | $CH_3$ | 2 |
| 52 | $4\text{-Cl—}3\text{-}NO_2\text{—}C_6H_3$ | $C_2H_5$ | $C_2H_5$ | 4 |
| 53 | $4\text{-t-}C_4H_9\text{—}C_6H_4$ | $CH_3$ | $CH_3$ | 4 |
| 54 | $4\text{-}C_4H_9O\text{—}C_6H_4$ | $CH_3$ | $CH_3$ | 4 |
| 55 | $4\text{-}C_4H_9O_2C\text{—}C_6H_4$ | $CH_3$ | $CH_3$ | 4 |
| 56 | $4\text{-}(C_6H_5CH_2)_2N\text{—}C_6H_4$ | $CH_3$ | $CH_3$ | 2 |
| 57 | $4\text{-}(C_4H_9)_2N\text{—}C_6H_4$ | $CH_3$ | $CH_3$ | 4 |

EXAMPLE 58

A solution containing 0.73 g. of the color former of Example 3 in 30 g. of isopropylbiphenyl and a solution containing 2.5 g. of carboxymethylcellulose in 100 ml. of water were mixed and emulsified by rapid stirring. The desired particle size (5 microns) was checked by microscope. To the emulsion was added a solution containing 7.5 g. of pigskin gelatin in 60 ml. of water. The pH was adjusted to 6.5 with 10% aqueous sodium hydroxide with rapid stirring, and following the gradual addition of 335 ml. of water at 50° C., the pH was adjusted to 4.5 with 10% aqueous acetic acid with continued rapid stirring. After 5 minutes the mixture was cooled to 15° C., treated with 10 g. of 25% aqueous glutaraldehyde and rapidly stirred for 15 minutes. The resulting microcapsule dispersion was stirred more slowly overnight, diluted with water to 560 g. and coated on white typewriter paper sheets. The sheets were air-dried. Duplicate typewritten images were made on receiving sheets coated with either phenolic resin or acidic clay. The color former of Example 3 produced an orange image on both types of receiving sheets.

EXAMPLE 59

To a solution prepared by dissolving 6.8 g. of terephthaloyl chloride in 37.1 g. of hot isopropylbiphenyl and then cooling to 30° C. was added a solution prepared by dissolving 2.1 g. of the color former of Example 1 in 34.3 g. of hot isopropylbiphenyl and then cooling to 40° C. The resulting mixture was slowly added to aqueous polyvinyl alcohol (prepared by diluting 5.9 g. of polyvinyl alcohol having a hydrolysis of 87 to 89% with 250 ml. of hot water, cooling to room temperature and further diluting with 40 ml. of water) and emulsified under high-shear agitation until a dispersed phase particle size of about 5 microns was obtained. The resulting emulsion was then stirred at conventional speed while adding a solution containing 2.2 g. of sodium carbonate and 3.9 g. of diethylenetriamine in 23 ml. of water. After stirring at room temperature for approximately 24 hours, the pH was adjusted to 7.3 with 15% aqueous sodium carbonate and the total weight of the suspension was adjusted to 326 g. by adding water if necessary. The resulting microcapsule suspension was then applied to a bond paper sheet (transfer sheet) and the coated sheet air-dried. The coated side of the transfer sheet was placed in contact with a receiving sheet coated with acidic clay. Writing on the transfer sheet produced an orange duplicate image on the receiving sheet.

EXAMPLE 60

A polyvinyl alcohol dispersion of the color formers of Examples 2 and 31 were prepared by shaking 1 hour on a paint shaker a mixture containing 2.0 g. of the color former, 3.7 g. of water, 8.6 g. of 10% aqueous polyvinyl alcohol and 10 ml. of zirconium grinding beads. Meanwhile a polyvinyl alcohol dispersion of bisphenol A was prepared by shaking a mixture containing 9.8 g. of bisphenol A, 18.2 g. of water, 42 g. of 10% aqueous polyvinyl alcohol and 70 ml. of zirconium grinding beads. The coating mixture was made by combining and thoroughly mixing 2.1 g. of the polyvinyl alcohol dispersion of the color former with 47.9 g. of the polyvinyl alcohol dispersion of bisphenol A. The coating mixture was applied to white mimeo paper sheets and the sheets were dried at room temperature. Contacting the coated sheets with a heated stylus at a temperature between 100°–150° C. produced a yellow image on the sheet coated with the color former of Example 2 and an orange image on the sheet coated with the color former of Example 31.

EXAMPLE 61

A starch paste was prepared by stirring a mixture containing 15.2 g. of low-viscosity oxidized starch (sold under the tradename STAYCOM by A. E. Staley Manufacturing Co.) and 60.0 g. of distilled water at room temperature until the mixture became homogeneous. The mixture was heated with stirring at 90°–93° C. for twenty minutes and then cooled to room temperature whereupon the resulting starch paste formed a gel. A starch dispersion of the color former of Example 1 was then prepared by shaking 0.5 hr. on a paint shaker a mixture containing 3.3 g. of the starch paste, 4.0 g. of the color former, 16 g. of distilled water, 17 g. of glass shot and 4.0 g. of a solution prepared by combining 30 g. of anhydrous disodium phosphate and 5.6 g. of sodium hydroxide in 100 g. of distilled water. Meanwhile a benzoyl peroxide dispersion was prepared by homogenizing for 0.5 hr. a mixture containing 32.6 g. of the starch paste, 11.2 g. of low-viscosity oxidized starch, 5.2 g. of benzoyl peroxide, 21.6 g. of distilled water, 20 ml. of glass shot and 27 g. of a solution prepared by combining 5.6 g. of sodium hydroxide and 30 g. of anhydrous disodium phosphate in 100 g. of distilled water. A paper coating mixture was prepared by combining and thoroughly mixing 14.5 g. of the starch dispersion of the color former with 26.2 g. of the starch dispersion of benzoyl peroxide. The resulting mixture was applied to white mimeo paper sheets and the sheets were dried at room temperature. Contacting the sheets with a heated stylus at a temperature between 100°–150° C. produced an orange image.

We claim:

1. A pressure-sensitive carbonless duplicating system or thermal marking system containing a support sheet coated with a color-forming substance comprising a compound having the formula

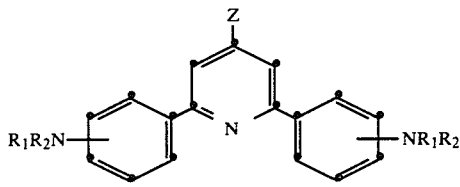

wherein:

$R_1$ and $R_2$ are the same or different and are selected from the group consisting of lower-alkyl and benzyl, or $NR_1R_2$ is pyrrolidinyl, piperidinyl, or morpholinyl;

Z is naphthyl, 9-julolidinyl or a substituent having the formula

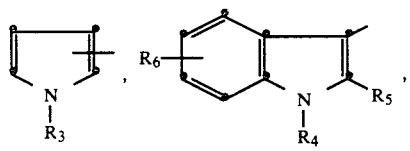

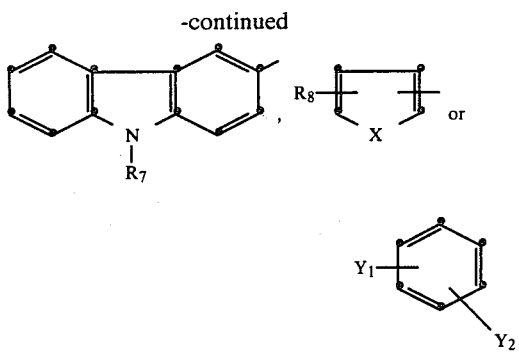

wherein $R_3$, $R_4$, $R_7$ and $R_8$ are hydrogen or non-tertiary lower-alkyl;

$R_5$ is hydrogen, phenyl or non-tertiary lower-alkyl;

$R_6$ is hydrogen, non-tertiary lower-alkyl or non-tertiary lower-alkoxy;

X is O or S;

$Y_1$ and $Y_2$ are the same or different and are selected from the group consisting of hydrogen, lower-alkyl, lower-alkoxy, halo, nitro, lower-alkoxycarbonyl, phenyl or $NR_9R_{10}$;

$R_9$ is lower-alkyl or benzyl;

$R_{10}$ is lower-alkyl, benzyl, cyano-lower-alkyl, or $NR_9R_{10}$ is pyrrolidinyl, piperidinyl, morpholinyl or isoindolinyl.

2. A pressure-sensitive carbonless duplicating system or a thermal marking system according to claim 1 wherein Z is a substituent having the formula

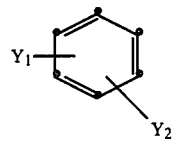

wherein $Y_1$ and $Y_2$ are the same or different and are selected from the group consisting of hydrogen, lower-alkyl, lower-alkoxy, halo, nitro, lower-alkoxycarbonyl, phenyl or $NR_9R_{10}$;

$R_9$ is lower-alkyl or benzyl;

$R_{10}$ is lower-alkyl, benzyl or cyano-lower-alkyl, or $NR_9R_{10}$ is pyrrolidinyl, piperidinyl, morpholinyl or isoindolinyl.

3. A pressure-sensitive carbonless duplicating system or thermal marking system according to claim 2 wherein $R_1$ and $R_2$ are each lower-alkyl and at least one of $Y_1$ and $Y_2$ is $NR_9R_{10}$ in which $R_9$ and $R_{10}$ are each lower-alkyl.

4. A pressure-sensitive carbonless duplicating system or thermal marking system according to claim 2 wherein $R_1$ and $R_2$ are each lower-alkyl and $Y_1$ and $Y_2$ are the same or different and are selected from the group consisting of hydrogen, lower-alkyl and lower-alkoxy.

5. A pressure-sensitive carbonless duplicating system or thermal marking system containing a support sheet coated with a color-forming substance comprising a blue or green and a red or orange color former in combination with a compound having the formula

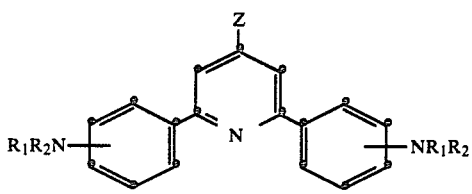

wherein:

R₁ and R₂ are the same or different and are selected from the group consisting of lower-alkyl and benzyl, or NR₁R₂ is pyrrolidinyl, piperidinyl, or morpholinyl;

Z is naphthyl, 9-julolidinyl or a substituent having the formula

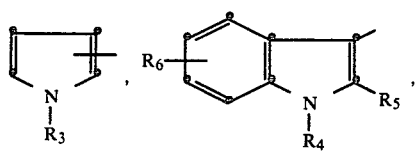

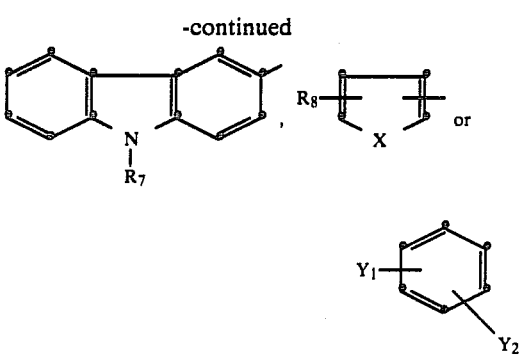

wherein

R₃, R₄, R₇ and R₈ are hydrogen or non-tertiary lower-alkyl;

R₅ is hydrogen, phenyl or non-tertiary lower-alkyl;

R₆ is hydrogen, non-teritary lower-alkyl or non-tertiary lower-alkoxy;

X is O or S;

Y₁ and Y₂ are the same or different and are selected from the group consisting of hydrogen, lower-alkyl, lower-alkoxy, halo, nitro, lower-alkoxycarbonyl, phenyl or NR₉R₁₀;

R₉ is lower-alkyl or benzyl;

R₁₀ is lower-alkyl, benzyl, cyano-lower-alkyl, or

NR₉R₁₀ is pyrrolidinyl, piperidinyl, morpholinyl or isoindolinyl.

* * * * *